United States Patent
Haller et al.

(10) Patent No.: US 11,432,820 B2
(45) Date of Patent: Sep. 6, 2022

(54) BAND LIGATION LOADING

(71) Applicant: United States Endoscopy Group, Inc., Mentor, OH (US)

(72) Inventors: Frederick Barclay Haller, Clemmons, NC (US); Melissa Hagerman Haller, Clemmons, NC (US)

(73) Assignee: UNITED STATES ENDOSCOPY GROUP, INC., Mentor, OH (US)

( * ) Notice: Subject to any disclaimer, the term of this patent is extended or adjusted under 35 U.S.C. 154(b) by 366 days.

(21) Appl. No.: 16/788,826

(22) Filed: Feb. 12, 2020

(65) Prior Publication Data

US 2020/0253610 A1    Aug. 13, 2020

Related U.S. Application Data

(60) Provisional application No. 62/804,567, filed on Feb. 12, 2019.

(51) Int. Cl.
*A61B 17/12* (2006.01)
*A61B 17/10* (2006.01)
*A61B 17/00* (2006.01)

(52) U.S. Cl.
CPC .. *A61B 17/12013* (2013.01); *A61B 17/00234* (2013.01); *A61B 2017/00876* (2013.01); *A61B 2017/12018* (2013.01)

(58) Field of Classification Search
CPC .. A61B 2017/12018; A61B 2017/0053; A61B 2017/00876; A61B 17/12009; A61B 17/12013; F16L 37/22; F16L 37/23
See application file for complete search history.

(56) References Cited

U.S. PATENT DOCUMENTS

| | | | |
|---|---|---|---|
| 6,565,578 B1 | 5/2003 | Peifer et al. | |
| 6,730,101 B1 | 5/2004 | Peifer et al. | |
| 2014/0100585 A1 | 4/2014 | Anderson et al. | |
| 2016/0007998 A1* | 1/2016 | Nobles | A61B 17/1204 606/153 |
| 2017/0290590 A1 | 10/2017 | Kamler | |
| 2017/0303930 A1 | 10/2017 | Haller et al. | |
| 2019/0296533 A1* | 9/2019 | Yeh | H02G 3/065 |

FOREIGN PATENT DOCUMENTS

| | | |
|---|---|---|
| WO | 2016/086003 A1 | 6/2016 |
| WO | 2019/147835 A1 | 8/2019 |
| WO | 2020/167925 A1 | 8/2020 |

* cited by examiner

*Primary Examiner* — Majid Jamialahmadi
(74) *Attorney, Agent, or Firm* — Calfee Halter & Griswold LLP (57) ABSTRACT

Methods, devices, and systems are provided herein for loading a band ligation barrel onto a surgical instrument. For example, a surgical system is provided for loading a band ligation barrel onto a surgical instrument that has a loading tube with a lumen to receive one or more band deployment cords of a band ligation barrel. The loading tube can be inserted through a first lumen of a surgical instrument. The system can also have a loading cap that receives a distal end of the loading tube, and a distal portion of the loading cap can be inserted into a distal-most opening of the band ligation barrel to secure band deployment cords therein. The system can also have a loading key that can be inserted into a second lumen of the surgical instrument, and a distal end of the loading key can engage with a proximal end of the loading tube.

14 Claims, 11 Drawing Sheets

BAND LIGATION LOADING

CROSS-REFERENCES

This application claims the benefit of priority to U.S. Provisional App. No. 62/804,567 of Haller et al., filed on Feb. 12, 2019 and entitled "Band Ligation Loading," which is incorporated herein by reference in its entirety.

FIELD

Surgical devices, systems, and methods are provided for loading band ligation instruments.

BACKGROUND

Band ligation of tissue is often performed using various band ligation instruments, such as endoscopic surgical devices. For example, one illustrative instrument can have an elongate shaft with at least one lumen therethrough and a ligation barrel disposed on a distal end thereof. The ligation barrel can have a plurality of ligation bands disposed around a radially outer surface thereof. The bands can be engaged with one or more beads on band deployment cords that extend distally along the radially outer surface of the ligation barrel, loop around a distal-most end of the ligation barrel, and extend proximally through the lumen of the elongate shaft to engage with an actuation mechanism on a proximal end thereof. In use, tissue is drawn into the ligation barrel, and proximal retraction of the band deployment cords is effective to eject the distal-most band from the barrel such that the band extends around and engages the tissue drawn into the ligation barrel. Additional tissue can be drawn into the ligation barrel and the band deployment cords can be further retracted to deploy additional bands.

During loading of the ligation barrel, the one or more cords need to be positioned to extend through the elongate shaft from the distal end to the proximal end thereof. Passing the one or more cords proximally through the lumen of the surgical instrument can require repeatedly passing various loading wires or members with hooks on distal ends thereof through an entire length of the lumen to engage the one or more cords and then to position proximal ends of the cords through the lumen, which can be difficult and time-consuming. Further complicating the loading process, many endoscopic surgical devices can have multiple lumens therethrough and/or various Y-connections therealong that allow for application of suction, fluid, passing of other surgical instruments therethrough, etc. Thus, a user can be required to navigate various lumens and channels with thin, difficult-to-maneuver loading devices while handling the band deployment cords which can twist and kink. Additionally, the distal end of the elongate shaft is inserted into a proximal end of the band ligation barrel after successfully translating the band deployment cords. Force applied to the elongate shaft and the band ligation barrel during loading can risk causing accidental deployment of one or more of the ligation bands thereon and/or causing damage to the barrel itself.

Therefore, improved band ligation loading techniques are needed.

SUMMARY

Methods, devices, and systems are provided herein for loading a band ligation barrel onto a surgical instrument.

In one aspect, a surgical system is provided for loading a band ligation barrel onto a surgical instrument, including a loading tube and a loading key. The loading tube has a proximal end, a distal end, and a lumen extending therebetween. The lumen receives one or more band deployment cords of a band ligation barrel, and the loading tube is inserted through a first lumen of a surgical instrument. The loading key has a proximal end and a distal end, and the loading key is inserted into a second lumen of the surgical instrument. The distal end of the loading key securably engages with the proximal end of the loading tube.

The surgical system can have numerous variations. For example, the surgical system can also include a loading cap that has a proximal portion with a lumen that removably receives the distal end of the loading tube therein. A distal portion of the loading cap is removably insertable into a distal-most opening of the band ligation barrel to secure the one or more band deployment cords therein relative to the band ligation barrel and to obstruct a deployment path of one or more ligation bands disposed on the band ligation barrel. In another example, the loading tube can be inserted into a distal end of the surgical instrument, and the loading key can be inserted into a proximal end of the surgical instrument. In still another example, the second lumen of the surgical instrument is in communication with the first lumen. The second lumen of the surgical instrument can also be different than the first lumen. In some examples, the distal end of the loading key can have a tapered portion. In other examples, at least one of the distal end of the loading key and the proximal end of the loading tube can be magnetic. In some embodiments, the distal end of the loading key can have at least one engagement means. The at least one engagement means can include a plurality of spherical structures, and the plurality of spherical structures can sequentially decrease in diameter from a proximal-most engagement means to a distal-most engagement means. In another example, the at least one engagement means comprises at least one spherical, ovular, or cylindrical structure. The distal end of the loading key can also be configured to be coaxially positioned within the second lumen. In some examples, the surgical instrument can be an endoscope.

In another aspect, a method of loading a band ligation barrel onto a surgical instrument is provided. The method includes inserting a distal end of a loading key into a proximal end of a first lumen of a surgical instrument. The method also includes inserting a proximal end of a loading tube into a distal end of a second lumen of the surgical device in communication with the first lumen and translating the loading tube proximally through the surgical instrument until the proximal end of the loading tube securely engages with the distal end of the loading key. The method further includes translating the engaged loading key and the loading tube proximally out of the first lumen of the surgical device.

The method can have a number of different variations. For example, the method can also include mating a band ligation barrel coupled to the distal end of the loading tube to a distal end of the surgical instrument, and the band ligation barrel can have at least one deployment cord engaged therewith and extending through the loading tube. In another example, translating the engaged loading key and the loading tube proximally can cause the distal end of the loading tube to decouple from the band ligation barrel and the at least one deployment cord to remain extending through the surgical instrument and engaged with the band ligation barrel. In still another example, the method can also include engaging proximal ends of the at least one deployment cord with a band deployment actuator on a proximal end of the surgical instrument such that the one or more cords are in condition to deploy a plurality of ligation bands from the band ligation barrel. The method can also include removing a loading cap from frictional engagement with the band ligation barrel in which the at least one deployment cord is initially in frictional engagement with the loading cap in the band ligation barrel. In another example, engagement between the loading tube and the loading key can be caused by at least one of frictional engagement or magnetic engagement between the loading tube and the loading key. In still another example, the distal end of the loading key can have at least one of a tapered portion or a plurality of spherical structures, and the plurality of spherical structures can sequentially decrease in diameter from a proximal-most engagement means to a distal-most engagement means.

BRIEF DESCRIPTION OF DRAWINGS

The embodiments described above will be more fully understood from the following detailed description taken in conjunction with the accompanying drawings. The drawings are not intended to be drawn to scale. For purposes of clarity, not every component may be labeled in every drawing. In the drawings.

DETAILED DESCRIPTION

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

Various exemplary methods, devices, and systems are provided for loading a band ligation barrel onto a surgical instrument, such as an endoscopic surgical device. The band ligation loading system can simplify the loading process by enabling band deployment cords to be translated through a surgical device without requiring various loading members to be passed both distally and proximally. It can also prevent tangling of the band deployment cords during loading, and can secure the band deployment cords and ligation bands during loading to prevent or limit accidental band deployment. In one exemplary embodiment, a loading system is provided having a loading tube, a loading cap, and a loading key. The loading tube can be sized and shaped to be inserted into a distal open and translated proximally along one or more lumens of a surgical instrument to pass one or more deployment cords of a band ligation barrel therethrough. The loading cap can be removably insertable into a distal opening of the band ligation barrel and can receive a distal end of the loading tube therein. As such, the loading cap can secure the one or more deployment cords therein during loading. The loading key can be insertable into a proximal opening and advanced distally through one of a plurality of lumens of the surgical instrument to engage with and guide the loading tube proximally into the one of the plurality of lumens when the loading tube is inserted into the surgical instrument during loading. For example, the loading key can serve to guide the loading tube through a Y-shaped channel in a handle of the endoscopic surgical device so as to easily allow the deployment cords to be passed through the Y-shaped channel without requiring various loading members to be passed both distally and proximally therethrough.

Figure 1:
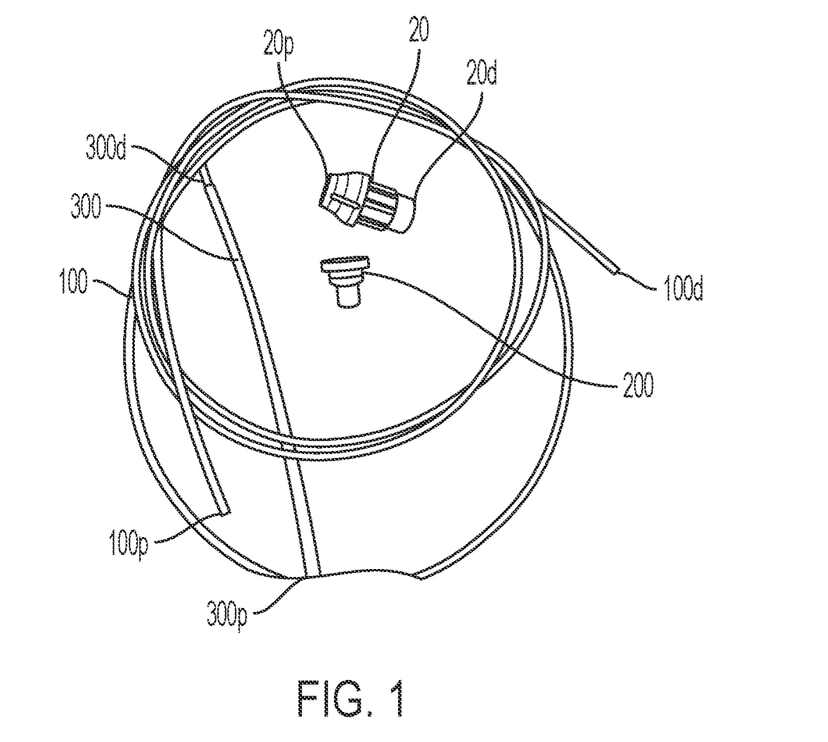
FIG. 1 is a top-down perspective view of one embodiment of a system for loading a band ligation barrel onto a surgical instrument.

FIG. 1 illustrates one embodiment of a band ligation loading system with a loading tube 100, a loading cap 200, and a loading key 300. Loading tube 100 is sized and shaped to be inserted into a distal opening and advanced proximally along one or more lumens of a surgical instrument to pass one or more band deployment cords 30a, 30b of a band ligation barrel 20 therethrough. It has an elongate shaft with proximal and distal ends 100p, 100d and a lumen therebetween that receives the one or more cords 30a, 30b therealong. The distal end 100d can be removably received in the loading cap 200 during loading, as discussed below. Furthermore, the proximal end 100p can receive a distal end of the loading key 300 therein and secure it thereto during loading, as discussed below. The loading tube 100 can have a longitudinal length that is greater than a length of one or more lumens of the surgical instrument into which it is inserted such that the loading tube 100 can protrude both distally and proximally from the surgical instrument. The loading tube 100 can be flexible but semi-rigid for insertion through various curved and/or angled channels of the surgical instrument, and it can be made from a variety of materials, such as plastics, polymers, etc. The loading tube 100 can be transparent such that the cords 30a, 30b are visible therethrough or it can be opaque to obscure viewing of the cords 30a, 30b.

Figure 2:
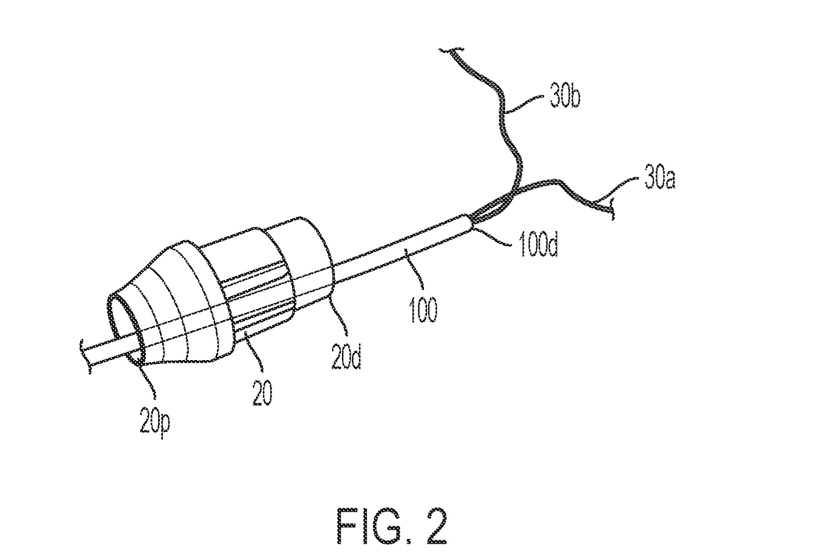
FIG. 2 is a perspective view of a loading tube, deployment cords, and a band ligation barrel of the system of FIG. 1.
Figure 3:
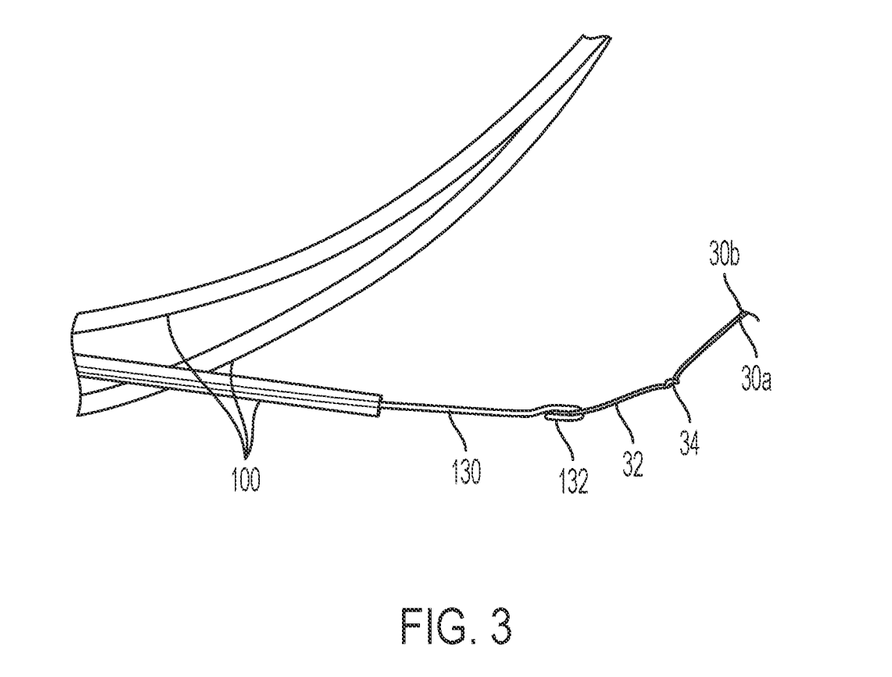
FIG. 3 is a perspective view of the loading tube, the deployment cords, and a loading hook of the system of FIG. 1 with a cord loading member.

The loading tube 100 can be pre-loaded with the one or more cords 30a, 30b to assist a user in loading the cords 30a, 30b through the surgical instrument. The cords 30a, 30b can be contained within the loading tube 100 until they have been extended through the surgical instrument and a user has withdrawn the tube from the surgical instrument, as discussed below. As such, there is minimal risk of the cords 30a, 30b twisting, tangling, kinking, knotting, etc. during placement and a user is not required to perform significant cord management, tie any knots or engagement points in the cords for engagement with the actuation mechanism, etc. As illustrated in FIGS. 2 and 3, the loading tube 100 can be pre-loaded with the one or more cords 30a, 30b using a variety of techniques, such as by using a loading wire 130 with a hook 132 on a distal end thereof. The loading wire 130 can be inserted from a proximal end to a distal end of the loading tube 100, engage with a proximal loop 32 and knot 34 of the one or more cords 30a, 30b, and be withdrawn proximally through the tube 100 so that the cords 30a, 30b are disposed therein. This can be achieved during manufacture such that a user receives the loading tube 100 with the cords 30a, 30b predisposed therein.

The loading cap 200 can secure the one or more cords 30a, 30b relative to the loading tube 100 and the band ligation barrel 20 during loading by a user to prevent or reduce any accidental ligation band deployment and cord twisting, as illustrated in FIGS. 2-7. The loading cap 200 can be removably insertable into a distal opening of the band ligation barrel 20 to secure the one or more cords 30a, 30b therein during loading. It can also receive the distal end 100d of the loading tube 100 (and thus ends of the cords 30a, 30b protruding distally from the tube 100) therein such that the tube 100 extends longitudinally through a lumen extending through the band ligation barrel 20. As such, the loading tube 100, the loading cap 200, and the band ligation barrel 20 can be removably coupled together during loading so that relative positions of the band ligation barrel 20 and the cords 30a, 30b are fixed. This prevents or reduces strain on the deployment cords 30a, 30b that might accidentally deploy one or more of a plurality of ligation bands 40 on the barrel 20 or twisting or fouling of the cords 30a, 30b during loading of the barrel 20 onto the surgical instrument.

Figure 4:
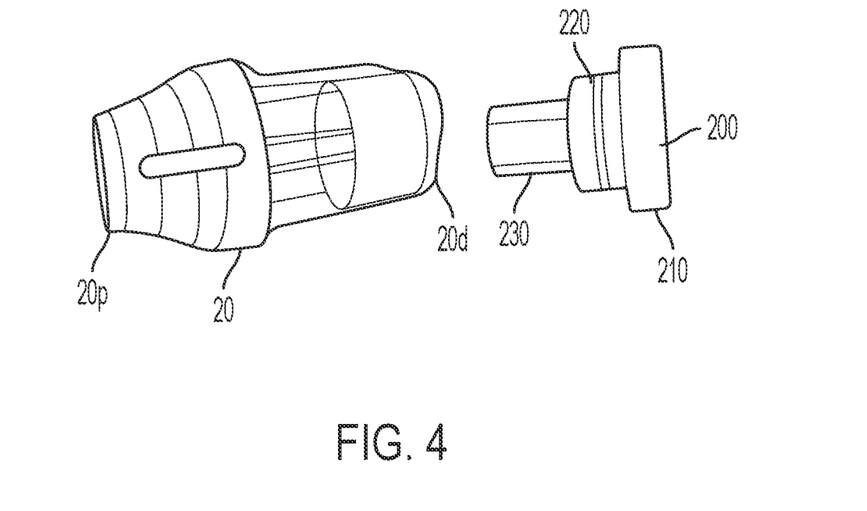
FIG. 4 is a side view of the band ligation barrel and a loading cap of the system of FIG. 1.
Figure 5:
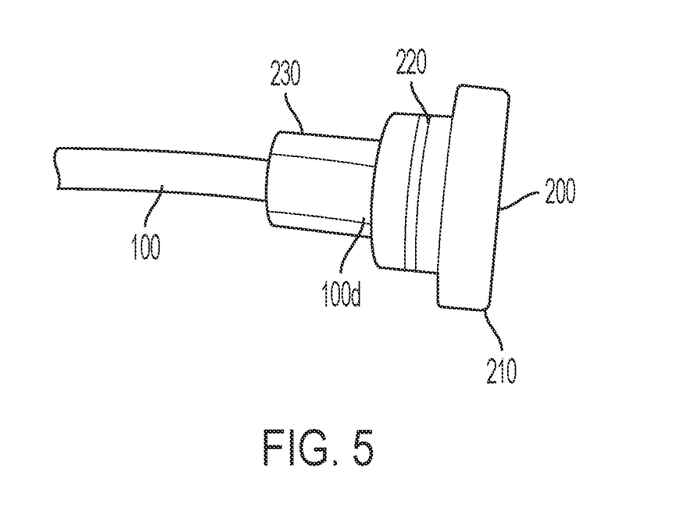
FIG. 5 is a side view of the loading tube and the loading cap of the system of FIG. 1.
Figure 6:
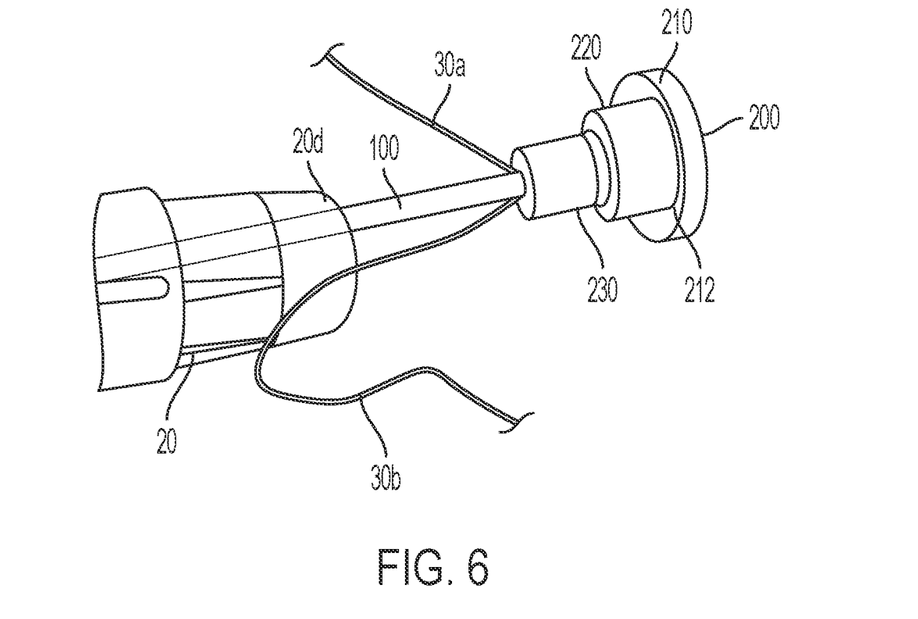
FIG. 6 is a perspective view of the band ligation barrel, the loading tube, the loading cap, and the deployment cords of the system of FIG. 1.
Figure 7:
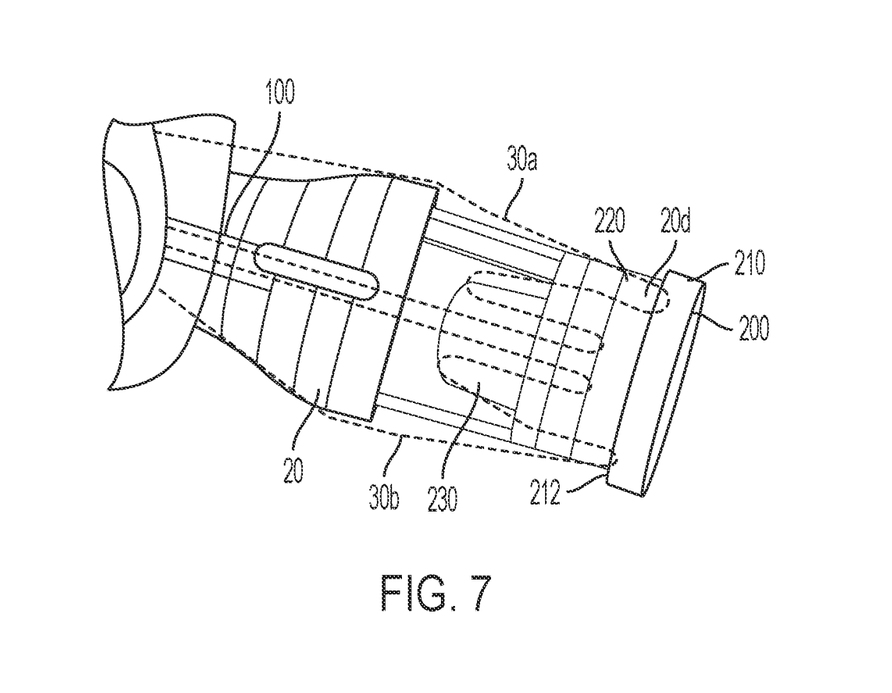
FIG. 7 is a side view of the band ligation barrel, the loading tube, the loading cap, and deployment cords of the system of FIG. 1.

In an exemplary embodiment, the loading cap 200 has a distal lip 210, a middle stopper 220, and a proximal receiver 230, as illustrated in FIGS. 4-6. The distal lip 210 receives a distal-most end 20d of the band ligation barrel 20 therein, and it has a ring structure with a groove or channel 212 into which the distal-most end 20d can be received. As such, the distal lip 210 can at least partially extend proximally along the inner and outer radial surfaces of the band ligation barrel 20 at the distal-most end 20d. The distal-most end 20d is thus enveloped in and protected by the distal lip 210. Furthermore, the distal lip 210 can apply secure frictional engagement to the one or more cords 30a, 30b that loop around the distal-most end 20d to prevent or reduce cord twisting or accidental ligation band deployment. If a ligation band 40 accidentally deploys during loading, the distal lip 210 can obstruct a distal deployment path of the band 40 to retain it on the barrel 20 because the distal lip 210 has a larger radial diameter than the distal-most end 20d. The middle stopper 220 protrudes proximally from the distal lip 210 and is inserted proximally into the distal opening defined by the distal-most end 20d of the band ligation barrel 20. As such, it fills the opening and occludes at least a distal portion of the lumen extending through the band ligation barrel 20. It has a cylindrical shape with a radial diameter that fits in a secure engagement against an inner radial surface of at least the distal end of the lumen of the barrel 20 so that it provides secure frictional engagement to the cords 30a, 30b extending therealong, thereby preventing movement of the cords 30a, 30b. The proximal receiver 230 protrudes proximally from the middle stopper 220 and has a lumen that removably receives the distal end 100d of the tube 100 in a secure frictional engagement when the tube 100 is inserted to extend longitudinally through the barrel 20 during loading. The lumen terminates at the middle stopper 220. The loading cap 200 can be made from a variety of materials, such as plastics, polymers, etc., and it can be transparent or opaque.

As indicated above, the loading cap 200 can be inserted into the band ligation barrel 20 to secure the cords 30a, 30b against the barrel 20 at several locations as the cords 30a, 30b extend along the tube 100, the cap 200, and the barrel 20. In particular, the cords 30a, 30b have a proximal end disposed within the tube 100, and have a distal end positioned proximal of a proximal-most band. The cords 30a, 30b follow a path that extends distally from the distal end 100d of the tube 100, and proximally around the distal end 100d of the tube 100. They are held in frictional engagement between the distal end 100d of the tube 100 and a proximal-most surface of the middle stopper 220. They further extend proximally along and are held in frictional engagement between an outer radial surface of the tube 100 and the inner radial surface of the lumen of the proximal receiver 230. The cords 30a, 30b then extend proximally and then distally around a proximal end of the proximal receiver 230 and are held in frictional engagement between the outer radial surface of the middle stopper 220 and the inner radial surface of the lumen of the band ligation barrel 20. The cords 30a, 30b then extend distally and then proximally around the distal-most end 20d of the barrel 20 and are held in frictional engagement between the distal-most end 20d and the distal lip 210. The cords 30a, 30b continue to extend proximally along the outer radial surface of the barrel 20 and extend through one or more ligation bands 40, with a terminal end of the cords 30a, 30b positioned just proximal to a proximal-most ligation band (not shown). Thus, a pathway of each cord 30a, 30b from the distal end 100d of the tube 100 to engagement with the ligation bands 40 on the outer radial surface of the barrel 20 follow an approximate S shape, as illustrated by superimposed lines in FIG. 7.

Figure 8:
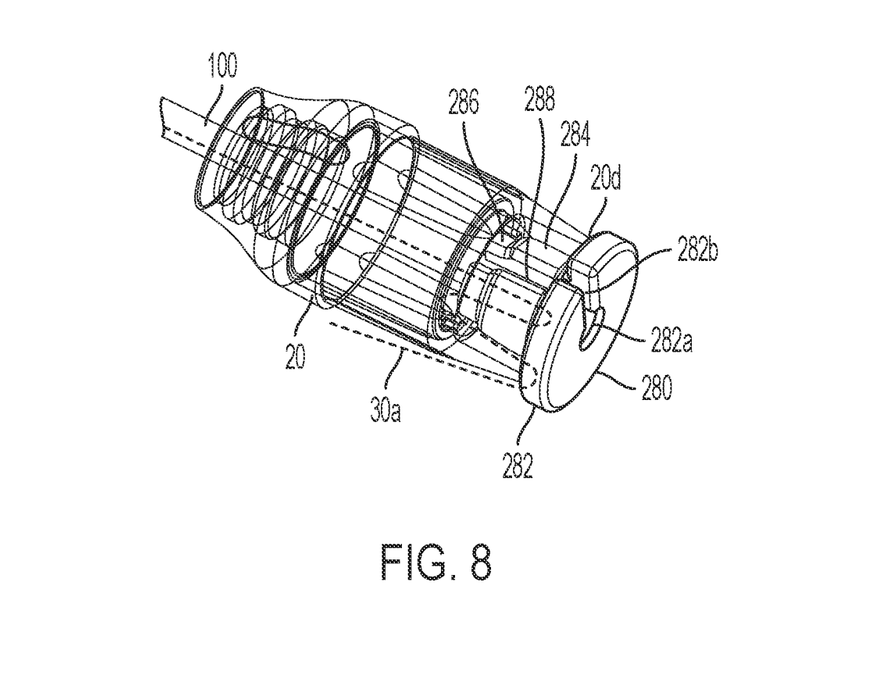
FIG. 8 is a partially-transparent view of another embodiment of a system for loading a band ligation barrel on a surgical instrument.

The loading cap can have a variety of different configurations. FIG. 8 illustrates another embodiment of a loading cap 280 similar to loading cap 200. Loading cap 280 secures one or more cords 30a relative to the loading tube 100 and the band ligation barrel 20 during loading, and it has a distal lip 282, a middle stopper 284, and a proximal receiver 286. The lumen that receives the distal end 100d of the tube 100 extends through both the proximal receiver 286 and the middle stopper 284 such that the one or more cords 30a extend distally from the tube 100 into frictional engagement with the distal lip 282. A channel 288 extends the lengths of the proximal receiver 286 and the middle stopper 284 and terminates in an opening 282a in a center of the distal lip 282 and connects with a channel 282b that extends between the opening 282a and an outer radial surface of the distal lip 282. The channels 288, 282b and opening 282a thus collectively form an approximate L shape through the loading cap 280 and allow for visualization of placement of the distal end 100d of the tube 100 in the loading cap 280. However, the channels 288, 282b and opening 282a are narrower than a diameter of the tube 100 such that the tube 100 can still be secured in the loading cap 280 in a frictional engagement.

Figure 9:
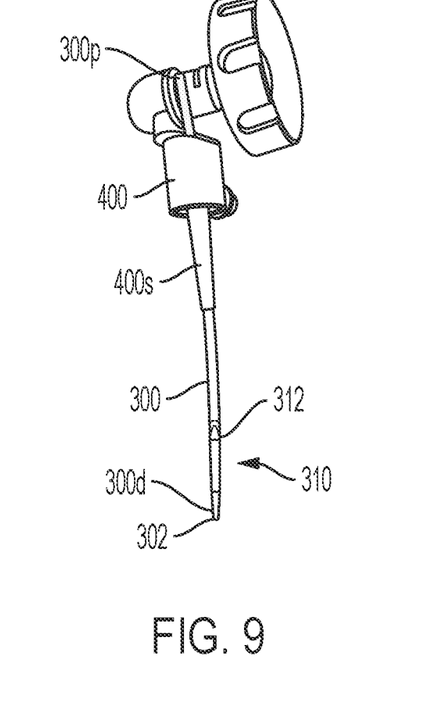
FIG. 9 is a perspective view of a loading key of the system of FIG. 1 with a handle.
Figure 10A:
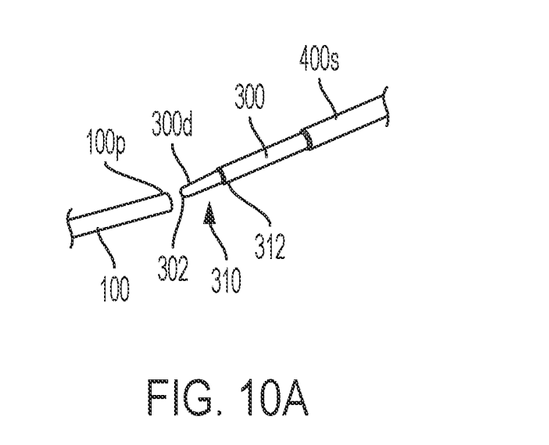
FIG. 10A is a perspective view of the loading key and the loading tube of the system of FIG. 1.
Figure 10B:
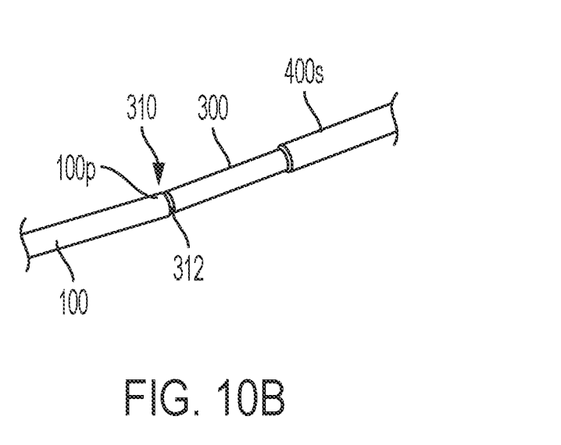
FIG. 10B is a perspective view of the loading key and the loading tube of the system of FIG. 1.

As indicated above, the loading system also includes a loading key 300 which is insertable distally through various ligation actuation mechanisms, such as through a lumen in a handle 400, and through one or more lumens of the surgical instrument to engage with and guide the loading tube 100 proximally along the one or more lumens when the loading tube 100 is inserted into the surgical instrument during loading. For example, the loading key 300 can serve as a guide to the loading tube 100 through a Y-shaped connection in the handle of the surgical instrument, as discussed below. In an exemplary embodiment, the loading key 300 is in the form of an elongate shaft having a distal end 300d that protrudes distally out of a lumen extending through the handle 400 and a handle stem 400s, and a proximal end 300p that protrudes proximally from the lumen of the handle 400. The distal end 300d of the key 300 can be configured engage with the proximal end 100p of the tube 100 as the tube 100 is inserted into the distal end and advanced proximally through the surgical device. As illustrated, the distal end 300d is tapered, narrowing to a distal-most point 302. The taper functions to center the distal-most point 302 of the key 300 approximately along a central longitudinal axis of the surgical instrument lumen so that the key 300 and the surgical instrument lumen are approximately coaxial. When the proximal end 100p of the tube 100 is advanced toward the loading key 300 during loading, the tapered point of the distal end 300d will enter the opening in the proximal end 100p of the tube 100 and can thus guide a distal portion 310 of the key 300 into a proximal portion of the lumen of the tube 100. In some embodiments, as the tube 100 continues to be inserted proximally, the distal portion 310 of the key 300 can enter the proximal portion of the tube 100 in a secure frictional fit such that the key 300 and the tube 100 engage to function as a single, unitary tube, as illustrated in FIGS. 10A and 10B. The loading key 300, when joined to the tube 100, is thus pushed proximally with continued proximal insertion of the tube 100 and acts as a guide for the proximal end 100p of the tube 100 by guiding it along the key's insertion path. The loading key 300 thus guides the tube 100 proximally out of the lumen of the surgical instrument and proximally out of the lumen of the handle 400. Such a configuration is particularly advantageous where the lumen extending through the surgical instrument is Y-shaped within the handle, as the key 300 can guide the loading tube 100 into a desired proximal lumen when the tube encounters a junction in the lumen. The loading key 300 can also guide initial insertion of the stem 400s of the handle 400 through various ports, biopsy valves, etc. of the surgical instrument.

As indicated above, the distal portion 310 of the key 300 is tapered and can thus proximally radially expand from the distal-most point 302 to a stepped portion 312 that has an outer diameter that corresponds to an outer diameter of the tube 100. As such, once the proximal portion of the tube 100 is fully advanced over the distal portion 310 of the key 300, the outer diameter of the tube 100 will abut the stepped portion 312. The tube 100 will engage the tapered portion of the key 300 and the outer diameter of the tube 100 and outer diameter of the key 300 will form a smooth outer surface to avoid catching or engaging on any instrument surfaces or elements during further proximal movement.

The distal portion 310 can be made of a softer or more flexible material than the remaining key 300 to provide further secure engagement between the key 300 and the tube 100, and in some embodiments, the distal portion 310 can at least slightly dilate the proximal portion of the tube 100 upon insertion therein. In some embodiments, the loading key 300 can have a sufficient length such that, upon initial placement in the handle 400 and the surgical instrument, the key 300 extends distally through a Y-shaped connector in the handle of the surgical instrument. The distal portion 310 can thus extending distally beyond a junction of the Y-lumen to receive and engage the tube 100 and guide the tube 100 through the Y-connector and proximally out of the handle 400, as discussed below. The loading key 300 can be made from a variety of materials, such as plastics, polymers, etc., and it can be transparent or opaque.

Figure 11A:
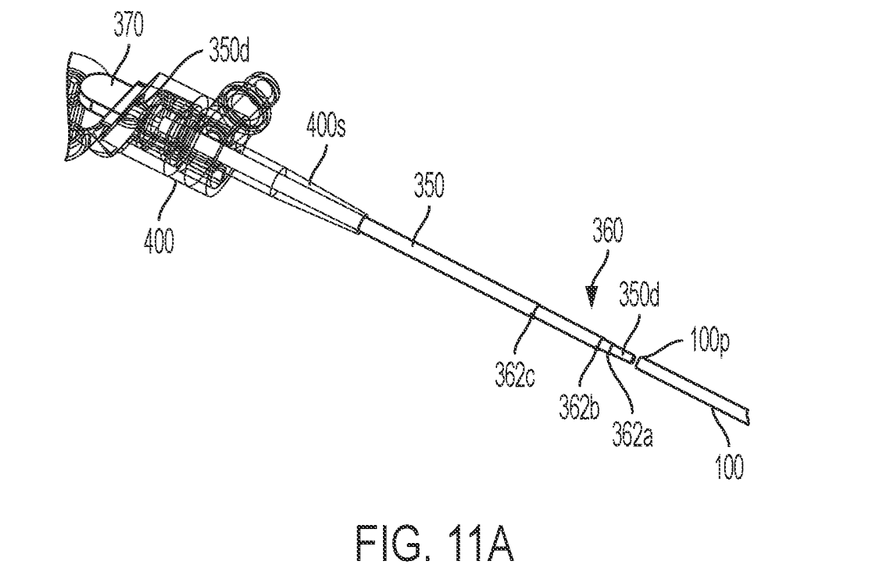
FIG. 11A is a partially-transparent perspective view of another embodiment of a system for loading a band ligation barrel onto a surgical instrument.

Various other embodiments of a loading key are possible. For example, FIG. 11A illustrates another embodiment of a loading key 350 similar to loading key 300. Loading key 350 can extend through the handle 400 and through one or more lumens of the surgical instrument. Loading key 350 has a distal barrel 370 on a proximal end 350p thereof that can rest against a proximal end of the lumen through the handle 400 and/or a proximal surface of the handle 400. When the key 350 and the handle 400 are initially positioned in a surgical instrument during loading, the distal barrel 370 can position a distal end 350d of the loading key 350 at a predetermined distance from the proximal opening. For example, in some embodiments, the surgical instrument can have a Y-lumen extending therethrough, with the distal portion of the lumen slitting at a junction into two proximal lumens. The length of the loading key 350 can be configured such that, when the proximal barrel 370 rests against the handle 400 upon full insertion of the loading key 350, the key 350 extends through the handle 400, past the junction of the Y lumen of the surgical instrument, and into the distal lumen. A distal portion 360 of the loading key 350 can receive and engage the tube 100 during proximal advancement of the tube 100 into the lumen and it can guide the tube 100 proximally through the junction of the Y lumen and out of the handle 400.

The distal portion 360 can have a plurality of stepped regions 362a, 362b, 362c with each having an outer diameter that corresponds to a different outer diameter of a loading tube such that tubes of different diameters can be used with one key. As such, loading tubes with internal diameters of different sizes can be selected depending on an internal diameter of a combined channel in a surgical device, such as a diagnostic endoscope and/or a therapeutic endoscope, without requiring multiple loading keys. In other embodiments, each stepped region 362a, 362b, 362c can provide a further dilation and engagement point along the distal portion 360 as the tube 100 is advanced over the distal portion 360. The proximal-most stepped region 362c can have an outer diameter that is the same as the outer diameter of the tube 100, similar to stepped region 312.

Figure 11B:
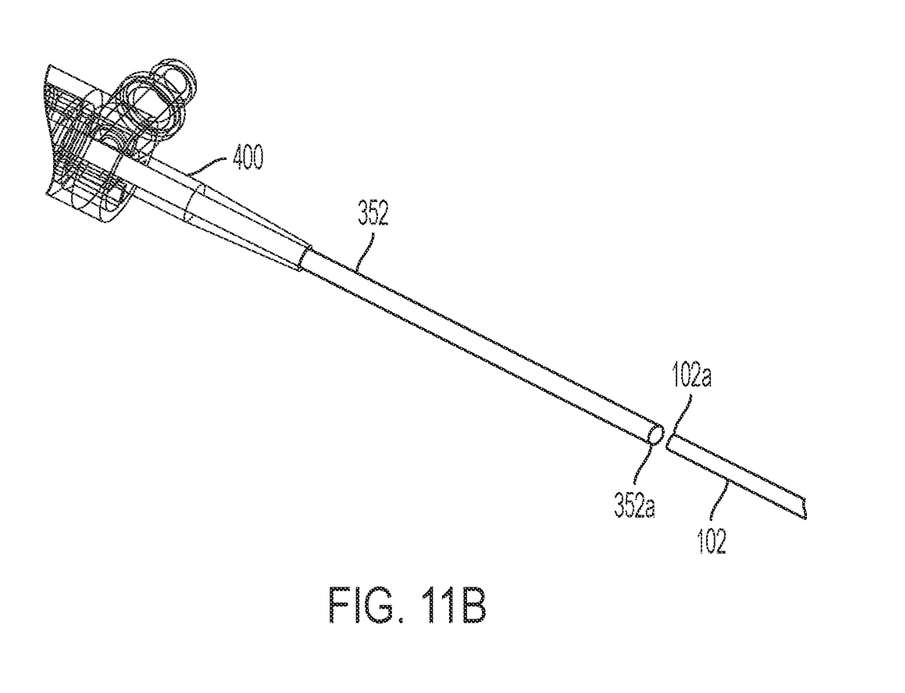
FIG. 11B is a partially-transparent perspective view of still another embodiment of a system for loading a band ligation barrel onto a surgical instrument.

Numerous other embodiments of loading key(s) and/or loading tube(s) can also be provided that have a variety of different connection interfaces between each corresponding key and tube in which the loading key is not tapered. FIG. 11B illustrates an embodiment of a loading key 352 similar to loading key 300 and a loading tube 102 similar to loading tube 100. Loading key 352 can extend through the handle 400 and through one or more lumens of the surgical instrument to engage the tube 102, which can be proximally advanced into the lumen. Loading key 352 has a magnetic component 352a at a distal end thereof, and the loading tube 102 has a magnetic component 102a at a proximal end thereof. The magnetic components 352a, 102a can be magnets of opposite polarity, or one component can be magnetic while the other component can be a material that is magnetically attracted, such as various metals, metallic alloys, etc. When the loading key 352 engages the tube 102, the magnetic components 352a, 102a can thus engage one another to allow the key 352 to guide the tube 102 proximally through the junction of the Y lumen and out of the handle 400. The magnetic components 352a, 102a provide a simple way to ensure engagement between the key 352 and the tube 102 during loading. The magnetic components 352a, 102a can take a variety of forms, such as being rectangular, circular, ring-shaped to surround the lumen of the tube 102, etc., and the components 352a, 102a can be embedded in the material used to make the loading key 352 and the tube 102 such that the components 352a, 102a themselves are not directly exposed to biological tissue, fluids, etc.

Figure 11C:
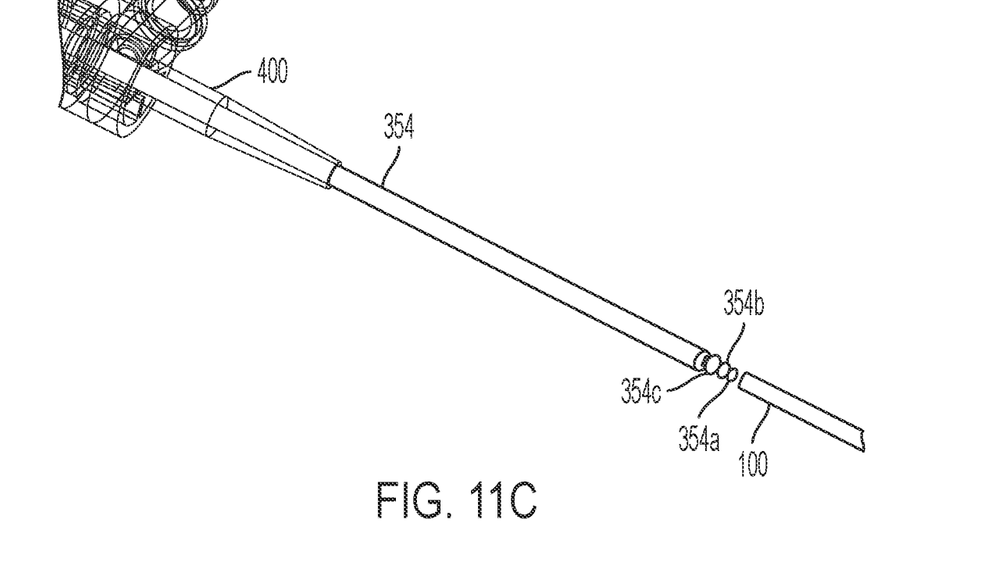
FIG. 11C is a partially-transparent perspective view of yet still another embodiment of a system for loading a band ligation barrel onto a surgical instrument.

FIG. 11C illustrates another embodiment of a loading key 354 similar to loading key 300 and the loading tube 100. Loading key 354 can extend through the handle 400 and through one or more lumens of the surgical instrument to engage the tube 100. Loading key 354 has one or more tube engagement means 354a, 354b, 354c at a distal end thereof that are received within the proximal end of the loading tube 100 during loading to cause the key 354 to engage the tube 100. The illustrated engagement means 354a, 354b, 354c are spherical structures that sequentially decrease in diameter from the proximal-most and largest engagement means 354c to the distal-most and smallest engagement means 354a. During loading, the smallest engagement means 354a is prevented from resting against an edge of the surgical instrument lumen because of the larger diameters of the engagement means 354b, 354c and the key 354, and instead, the engagement means 354a is positioned within a middle area along a central longitudinal axis of the surgical instrument lumen. This positioning ensures that the engagement means 354a is able to enter the opening in the proximal end of the tube 100 and can thus guide the subsequent engagement means 354b, 354c into the lumen of the tube 100. The engagement means 354a, 354b, 354c can then provide secure engagement between the key 354 and the tube 100 to allow easier loading. Other embodiments can have a different number of engagement means, such as one, two, four, five, etc., and the engagement means can have different shapes, such as ovular, cylindrical, etc.

Figure 12:
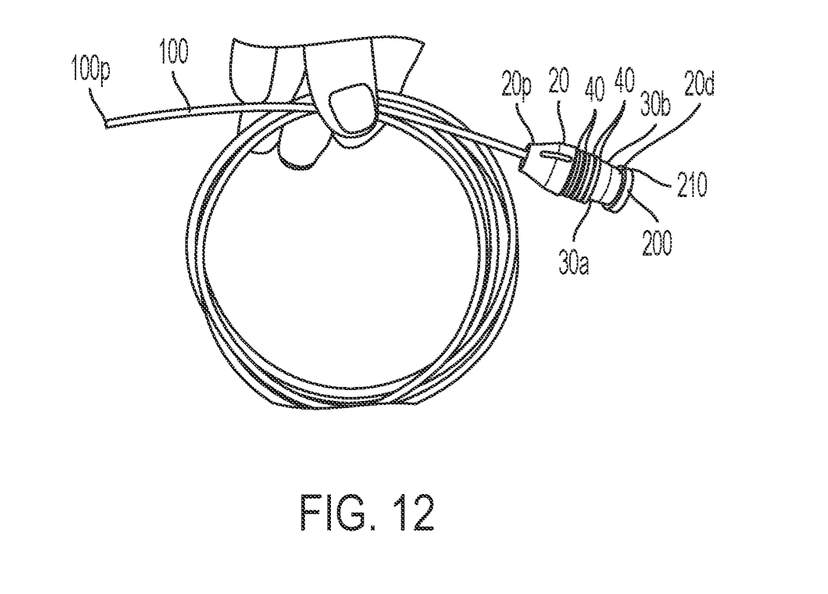
FIG. 12 is a top-down view of the loading system engaged with the band ligation barrel of FIG. 1.

In use, a kit can be provided to a user having the band ligation barrel 20, the tube 100, the loading cap 200, and the loading key 300. As illustrated in FIG. 12, the tube 100, the loading cap 200, and the band ligation barrel 20 can be pre-assembled such that the cords 30a, 30b extend through the tube 100, the distal end 100d of the tube 100 is passed longitudinally through the band ligation barrel 20 and engaged with the loading cap 200, and the loading cap 200 is inserted distally into the distal opening of the barrel 20 to secure the cords 30a, 30b. The plurality of ligation bands 40 can be pre-loaded onto the barrel 20 such that the cords 30a, 30b are disposed through each ligation band 40 along the outer radial surface of the barrel 20. The cords 30a, 30b can have one or more beads positioned thereon that engage each ligation band 40. Because the tube 100 and the band ligation barrel 20 can be provided to a user pre-engaged with one another, the user can simply insert the tube 100 proximally into the device 500, insert the key 300 distally into the device 500, and thus be able to rapidly and correctly load the device in preparation for use without difficulty. While the tube 100, the loading cap 200, and the band ligation barrel 20 are pre-assembled, in other embodiments one or more components can be assembled or adjusted by a user in an operating space. Additionally, the loading tube 100 can be pre-disposed to a coiled configuration and can be configured to maintain its coiled configuration during maneuvering and loading to assist in keeping the tube 100 from contacting any surfaces or interfering with the operating space.

Figure 13A:
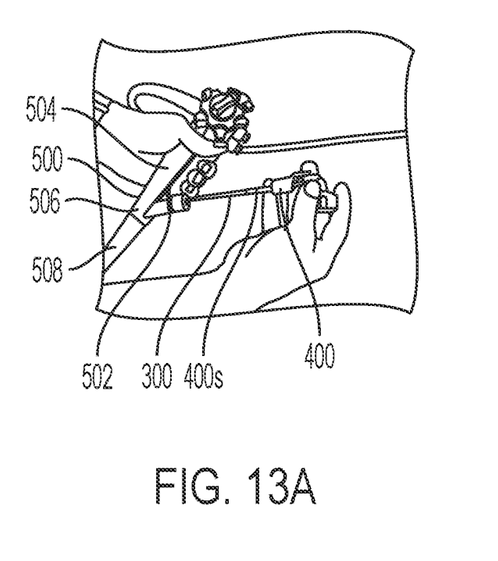
FIG. 13A is a perspective view of the loading system of FIG. 1 being loaded onto a surgical instrument.
Figure 13B:
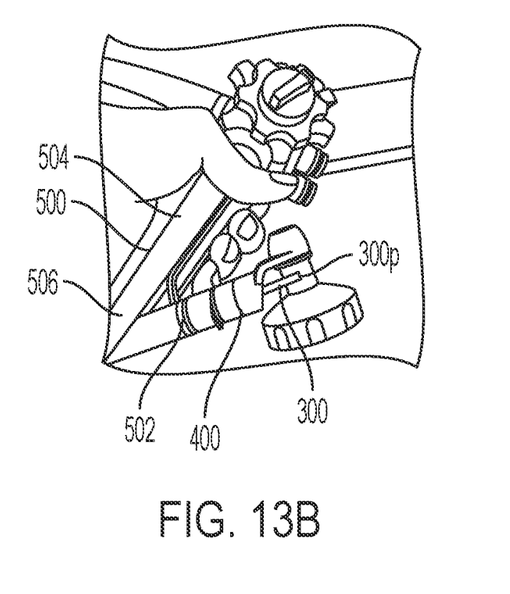
FIG. 13B is a perspective view of the loading system of FIG. 1 being loaded onto the surgical instrument of FIG. 12A.

To load the band ligation barrel 20 onto a surgical instrument, such as an endoscopic surgical device 500, in anticipation of band deployment, the loading key 300 can be inserted into the lumen of the handle 400, and the loading key 300 and the stem 400s of the handle 400 can both be inserted into an auxiliary channel 502 of the endoscopic surgical device 500, as illustrated in FIGS. 13A and 13B. The illustrated endoscopic surgical device 500 can have at least a main channel 504, the auxiliary channel 502, a combined channel 508, and a Y-connector 506 that merges the main channel 504 and the auxiliary channel 502 on a proximal end thereof into the combined channel 508 on a distal end thereof. The loading key 300 can assist in guiding placement of the stem 400s into the auxiliary channel 502 through any ports, biopsy valves, etc. therein. The loading key 300 can also be inserted distally into the auxiliary channel 502 through the lumen of the handle 400 until the key 300 extends through the auxiliary channel, the Y-connector 506, and into the combined channel 508 such that the distal end 300d of the key 300 protrudes at least partially into the combined channel 508. While the illustrated loading key 300 can be inserted to a variety of depths into the device 500, other embodiments of the loading key can be used herein with distal barrels similar to distal barrel 370 of the key 350 discussed above to control a desired insertion depth, such as to easily and controllably protrude at least partially into the combined channel 508 through the Y-connector 506. Additionally, while the endoscopic surgical device 500 is illustrated herein, a variety of surgical instruments can be used. The main channel 504 can also have various uses, such as allowing suction and/or fluid to be applied thereto, allowing tools to be inserted therealong, etc. The endoscopic surgical device 500 can also have a plurality of channels or lumens therethrough and can have an imaging device disposed therein such that imaging of an area distal to the device 500 is possible.

Figure 14:
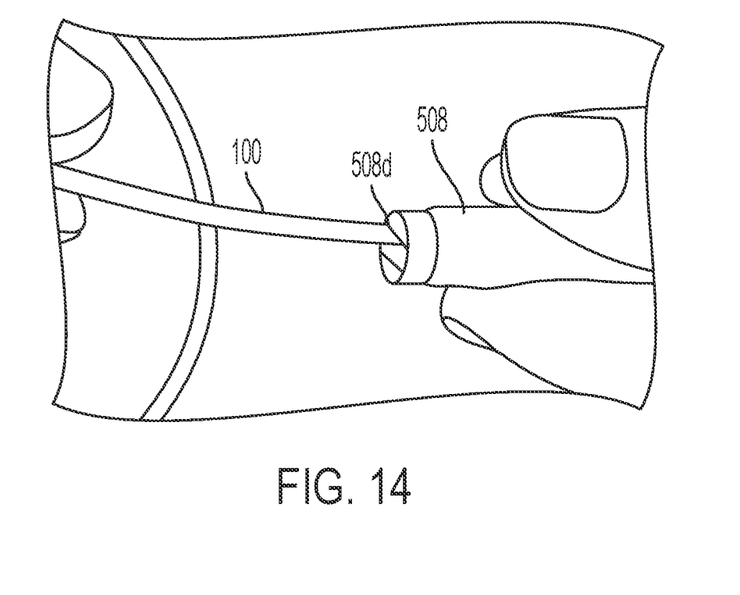
FIG. 14 is a perspective view of the loading system of FIG. 1 being loaded onto the surgical instrument of FIG. 12A.
Figure 15:
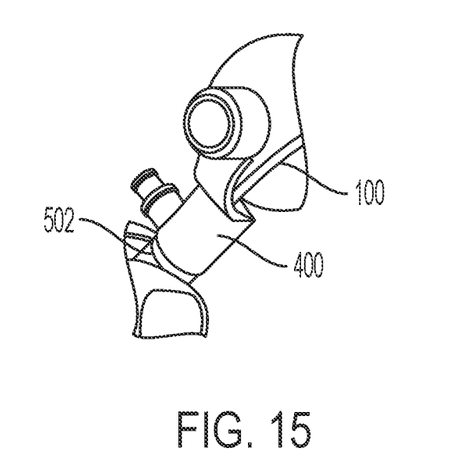
FIG. 15 is a perspective view of the loading system of FIG. 1 being loaded onto the surgical instrument of FIG. 12A.

The user can insert the proximal end 100p of the tube 100 into a distal end 508d of the combined channel 508 of the device 500, as illustrated in FIG. 14. The user can begin to advance or translate the tube 100 proximally within the combined channel 508 until the proximal end 100p of the tube 100 encounters the distal end 300d of the loading key 300 distal to the Y-connector 506. As discussed above, the two ends 100p, 300d can merge such that the distal end 300d extends into the proximal end 100p and engages the key 300 such that the key 300 and tube 100 are maneuvered as a single, unitary shaft. The user may feel the engagement between the two ends 100p, 300d based on tactile feedback on the tube 100. The user can continue to advance the joined tube 100 and loading key 300 until the key 300 and a proximal portion of the tube 100 extend proximally from the handle 400, as illustrated in FIG. 15. In the illustrated embodiment, the main channel 504 of the device 500 is coaxial with the combined channel 508, and the auxiliary channel 502 extends at a non-zero angle from the coaxial main and combined channels 504, 508. Thus, without the loading key 300, unguided proximal translation of the proximal end 100p of the tube 100 can result in the tube 100 passing through the Y-connector 506 and into the main channel 504 rather than the auxiliary channel 502. However, because the loading key 300 is initially inserted through the Y-connector 506 from the auxiliary channel 502 rather than the main channel 504 and extends therethrough when engagement is made, proximal translation of the combined loading key 300 and tube 100 relative to the device 500 follows the initial insertion path of the key 300 through the Y-connector 506 and through the auxiliary channel 502. The proximal end 100p of the tube 100 can thus avoid proximal insertion into the main channel 504 even when translation of the proximal end 100p must occur at a non-zero angle in the Y-connector 506 to successfully pass through the Y-connector 506 and into the auxiliary channel 502.

Figure 16A:
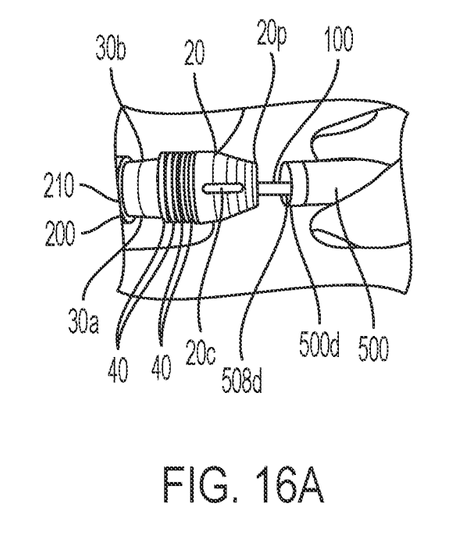
FIG. 16A is a side view of the band ligation barrel of FIG. 1 being loaded onto the surgical instrument of FIG. 12A.
Figure 16B:
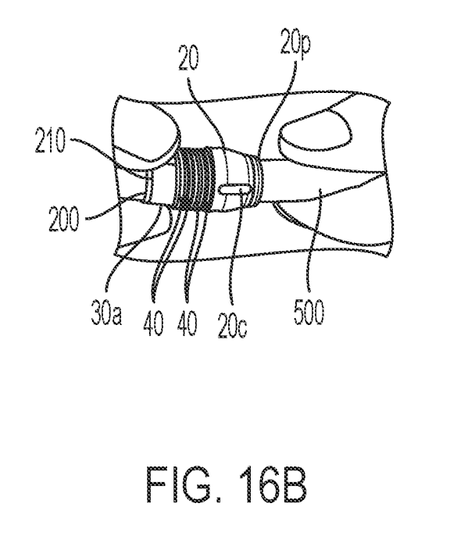
FIG. 16B is a side view of the band ligation barrel of FIG. 1 being loaded onto the surgical instrument of FIG. 12A.

As the proximal portion of the tube 100 extends proximally from the handle 400, the user can insert a distal end 500d of the device 500 into the proximal end 20p of the band ligation barrel 20 such that the barrel 20 and the device 500 engage in a secure frictional fit, as illustrated in FIGS. 16A and 16B. In some embodiments, an alignment indicator 20c in the form of a rectangular line on the band ligation barrel 20 can be aligned with the combined channel 508 during engagement of the barrel 20 and the device 500. For example, this alignment can be preferable in embodiments in which the device 500 has a plurality of lumens or channels therethrough that are not coaxial with one another and the cords 30a, 30b are arranged such that parallel alignment of the cords 30a, 30b through the combined channel 508 is preferred to ensure smooth translation of the cord 30a, 30b during band deployment.

Figure 17A:
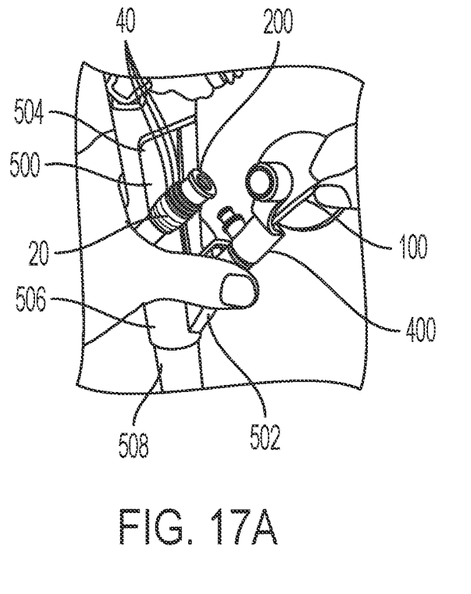
FIG. 17A is a perspective view of the loading system of FIG. 1 being loaded onto the surgical instrument of FIG. 12A.
Figure 17B:
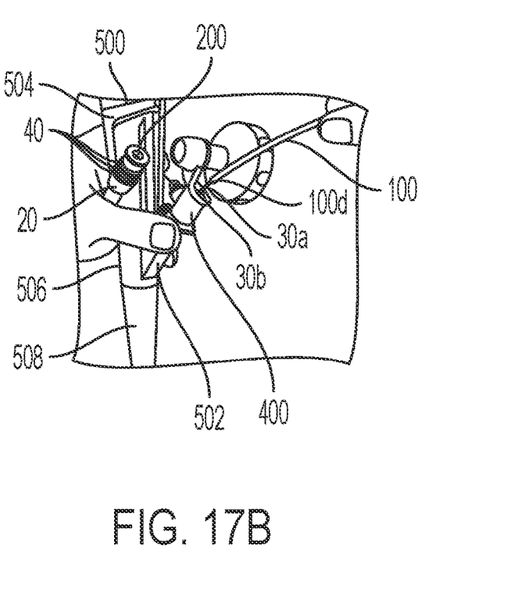
FIG. 17B is a perspective view of the loading system of FIG. 1 being loaded onto the surgical instrument of FIG. 12A.

When the barrel 20 is securely engaged with the distal end 500d of the device 500, such as by a friction fit, the user can grasp the loading key 300 and/or the proximal portion of the tube 100 protruding from the handle 400 and they can pull the combined key 300 and tube 100 proximally relative to the handle 400 and the device 500. The distal end 100d of the tube 100 is translated proximally out of frictional engagement with the proximal receiver 230 of the loading cap 200 upon application of the proximal pulling force because the barrel 20 is in engagement with the distal end 500d of the device 500 and retains the loading cap 200 therein. The distal end 100d of the tube 100 can continue to be translated proximally by the user through the barrel 20, the combined channel 508, the Y-connector 506, the auxiliary channel 502, and finally proximally out of the handle 400. As the distal end 100d is translated proximally, the cords 30a, 30b remain in frictional engagement with the barrel 20 because of the engagement points with the loading cap 200 and the ligation bands 40 on the band ligation barrel 20. Thus, proximal translation of the tube 100 causes the cords 30a, 30b to be withdrawn from the distal end 100d of the tube 100 and to remain extending along the combined channel 508, the Y-connector 506, the auxiliary channel 502, the handle 400, and finally proximally from the handle 400, as illustrated in FIGS. 17A and 17B.

Figure 18A:
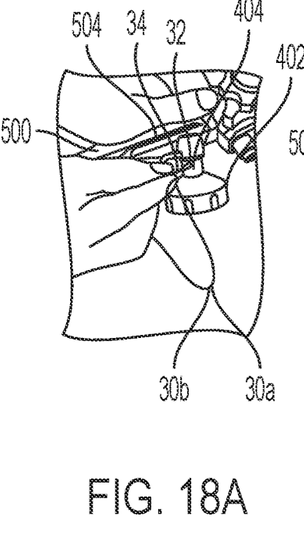
FIG. 18A is a perspective view of deployment cords engaged with the band ligation barrel of FIG. 1 being actuatably engaged with the surgical instrument of FIG. 12A.
Figure 18B:
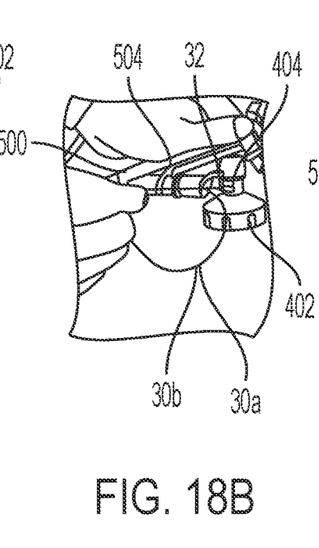
FIG. 18B is a perspective view of deployment cords engaged with the band ligation barrel of FIG. 1 being actuatably engaged with the surgical instrument of FIG. 12A.
Figure 18C:
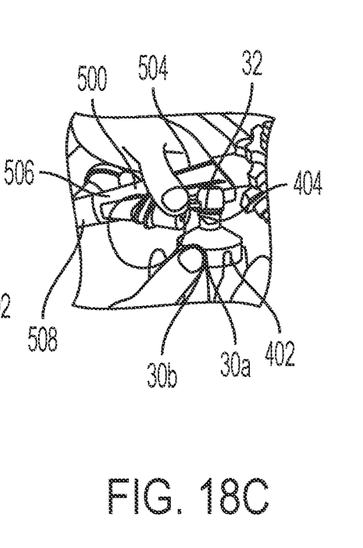
FIG. 18C is a perspective view of deployment cords engaged with the band ligation barrel of FIG. 1 being actuatably engaged with the surgical instrument of FIG. 12A.

When the one or more cords 30a, 30b are completely withdrawn from the tube 100, the loop 32 and the knot 34 joining the cords 30a, 30b on distal ends thereof are exposed. The user can engage the cords 30a, 30b with the handle 400 in preparation for actuation and band deployment. For example, the user can engage the loop 32 with a hook 404 disposed on a rotational spool 402 of the handle 400, and the user can rotate the rotational spool 402 to wrap the cords 30a, 30b therearound to remove excess cord, as illustrated in FIGS. 18A-18C. Thus, the loading key 300 allows the tube 100 to be loaded into the instrument from a distal-to-proximal direction through the Y-connector 506, rather than a proximal-to-distal direction, and allows fast and efficient loading to speed up the loading process and prevent or reduce accidents during the loading process.

Figure 19:
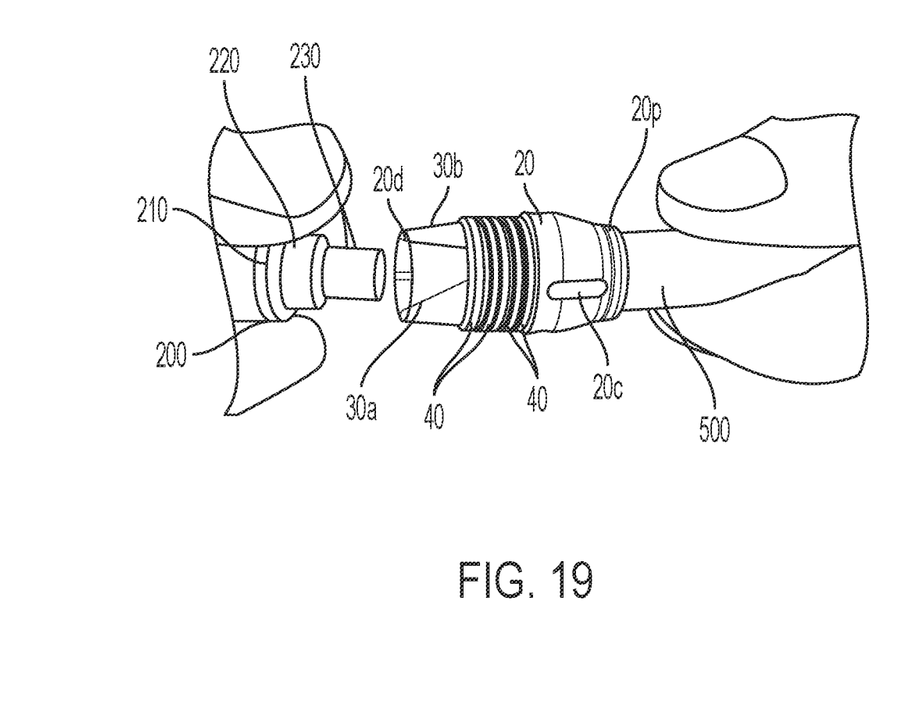
FIG. 19 is a side view of components of the system being removed from the band ligation barrel of FIG. 1 on the surgical instrument of FIG. 12A.

When the one or more cords 30a, 30b are engaged with the handle 400 and in condition for actuation, the loading cap 200 can be removed from the band ligation barrel 20, as illustrated in FIG. 19. After successfully loading the band ligation barrel 20 onto the surgical device 500, tissue ligation can proceed, for example as discussed in WIPO Patent Pub. No. WO2016/086003, entitled "Tissue Ligation Apparatus With A Rotating Spool Assembly And A Valve Assembly" and filed on Nov. 24, 2015 and WIPO Patent Pub. No. WO2019/147835, entitled "Anti-Slip Bands" and filed on Jan. 24, 2019, both of which are incorporated herein by reference in their entirety.

Thus, using one or more of the components of the loading system discussed herein, the band ligation barrel 20 can be loaded onto the distal end 500d of the endoscopic surgical device 500 and the one or more cords 30a, 30b can be extended through the device 500 for engagement with and eventual actuation by the handle 400 in a rapid and simple manner while avoiding or reducing cord entanglement and accidental band deployment.

All of the devices disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

One skilled in the art will appreciate further features and advantages of the described devices and methods based on the above-described embodiments. Accordingly, the present disclosure is not to be limited by what has been particularly shown and described, except as indicated by the appended claims. All publications and references cited herein are expressly incorporated herein by reference in their entirety.

What is claimed is:

1. A surgical system for loading a band ligation barrel onto a surgical instrument, comprising:
   a loading tube having a proximal end, a distal end, and a lumen extending therebetween, the lumen being configured to receive one or more band deployment cords of a band ligation barrel therethrough, and the loading tube being configured to be inserted through a first lumen of a surgical instrument; and
   a loading key having a proximal end and a distal end, the loading key being configured to be inserted into a second lumen of the surgical instrument, and the distal end of the loading key being configured to securably engage with the proximal end of the loading tube;
   wherein the distal end of the loading key has at least one engagement means;
   wherein the at least one engagement means comprises a plurality of spherical structures; and
   wherein the plurality of spherical structures sequentially decrease in diameter from a proximal-most engagement means to a distal-most engagement means of the at least one engagement means.

2. The surgical system of claim 1, further comprising a loading cap having a proximal portion with a lumen configured to removably receive the distal end of the loading tube therein and a distal portion configured to be removably insertable into a distal-most opening of the band ligation barrel to secure the one or more band deployment cords therein relative to the band ligation barrel and to obstruct a deployment path of one or more ligation bands disposed on the band ligation barrel.

3. The surgical system of claim 1, wherein the loading tube is configured to be inserted into a distal end of the surgical instrument, and the loading key is configured to be inserted into a proximal end of the surgical instrument.

4. The surgical system of claim 1, wherein the second lumen of the surgical instrument is in communication with the first lumen.

5. The surgical system of claim 1, wherein the second lumen of the surgical instrument is different than the first lumen.

6. The surgical system of claim 1, wherein the distal end of the loading key is configured to be coaxially positioned within the second lumen.

7. The surgical system of claim 1, wherein the surgical instrument is an endoscope.

8. A method of loading a band ligation barrel onto a surgical instrument, comprising:
   inserting a distal end of a loading key into a proximal end of a first lumen of the surgical instrument;
   inserting a proximal end of a loading tube into a distal end of a second lumen of the surgical instrument in communication with the first lumen and translating the loading tube proximally through the surgical instrument until the proximal end of the loading tube securely engages with the distal end of the loading key;
   translating the engaged loading key and the loading tube proximally out of the first lumen of the surgical instrument.

9. The method of claim 8, further comprising mating a band ligation barrel coupled to the a distal end of the loading tube to a distal end of the surgical instrument, the band ligation barrel having at least one deployment cord engaged therewith and extending through the loading tube.

10. The method of claim 9, wherein translating the engaged loading key and the loading tube proximally causes the distal end of the loading tube to decouple from the band ligation barrel and the at least one deployment cord to remain extending through the surgical instrument and engaged with the band ligation barrel.

11. The method of claim 9, further comprising: engaging proximal ends of the at least one deployment cord with a band deployment actuator on a proximal end of the surgical instrument such that the at least one deployment cord are in condition to deploy a plurality of ligation bands from the band ligation barrel.

12. The method of claim 9, further comprising:
   removing a loading cap from frictional engagement with the band ligation barrel, the at least one deployment cord initially in frictional engagement with the loading cap in the band ligation barrel.

13. The method of claim 8, wherein engagement between the loading tube and the loading key is caused by at least one of frictional engagement or magnetic engagement between the loading tube and the loading key.

14. The method of claim 8, wherein the distal end of the loading key has at least one of a tapered portion or a plurality of spherical structures, and the plurality of spherical structures sequentially decrease in diameter from a proximal-most engagement means to a distal-most engagement means.

* * * * *